United States Patent
Overett et al.

(10) Patent No.: US 8,461,406 B2
(45) Date of Patent: Jun. 11, 2013

(54) OLIGOMERISATION OF OLEFINIC COMPOUNDS IN THE PRESENCE OF A DILUTED METAL CONTAINING ACTIVATOR

(75) Inventors: Matthew James Overett, Johannesburg (ZA); Kevin Blann, Alberton (ZA); Esna Killian, Sasolburg (ZA); David Hedley Morgan, Sasolburg (ZA); Hulisani Maumela, Johannesburg (ZA); Annette Bollmann, Henley-on-Klip (ZA); John Thomas Dixon, Vanderbijlpark (ZA)

(73) Assignee: Sasol Technology (PTY) Limited, Johannesburg (ZA)

( * ) Notice: Subject to any disclaimer, the term of this patent is extended or adjusted under 35 U.S.C. 154(b) by 804 days.

(21) Appl. No.: 11/993,396

(22) PCT Filed: Jul. 10, 2006

(86) PCT No.: PCT/IB2006/052324
§ 371 (c)(1),
(2), (4) Date: May 14, 2010

(87) PCT Pub. No.: WO2007/007272
PCT Pub. Date: Jan. 18, 2007

(65) Prior Publication Data
US 2010/0222622 A1    Sep. 2, 2010

(30) Foreign Application Priority Data
Jul. 12, 2005  (ZA) .................................. 2005/05579

(51) Int. Cl.
*C07C 2/22*    (2006.01)

(52) U.S. Cl.
USPC ........... 585/513; 585/502; 585/510; 585/511; 585/512; 585/520; 585/521; 585/522; 585/523

(58) Field of Classification Search
USPC ................. 585/502, 510, 511, 512, 513, 520, 585/521, 522, 523
See application file for complete search history.

(56) References Cited

U.S. PATENT DOCUMENTS

| | | | |
|---|---|---|---|
| 5,523,507 A * | 6/1996 | Reagen et al. | 585/513 |
| 5,919,996 A * | 7/1999 | Freeman et al. | 585/513 |
| 6,166,154 A * | 12/2000 | Oskam et al. | 526/160 |
| 2004/0228775 A1* | 11/2004 | Ewert et al. | 422/131 |

(Continued)

FOREIGN PATENT DOCUMENTS

| | | |
|---|---|---|
| WO | WO 02/04119 A1 | 1/2002 |
| WO | WO 2004/056480 A1 | 7/2004 |

OTHER PUBLICATIONS

Krause, et al., "Aluminum Compounds, Organic" in Ullmann's Encyclopedia of Industrial Chemistry, Wiley-VCH, 2005, available on-line Jun. 15, 2000.*

(Continued)

*Primary Examiner* — In Suk Bullock
*Assistant Examiner* — Bradley Etherton
(74) *Attorney, Agent, or Firm* — Finnegan Henderson Farabow Garrett & Dunner LLP

(57) ABSTRACT

According to the present invention there is provided a process for producing an oligomeric product by the oligomerisation of at least one olefinic compound including: A) providing an activated oligomerisation catalyst comprising the combination of: i) a source of a transition metal; ii) a ligating compound of the formula $(R^1)_m X^1(Y) X^2(R^2)_n$ iii) a metal containing activator; and (iv) at least one olefinic compound; B) diluting the activated oligomerisation catalyst of A with an introduced liquid medium; and C) contacting the at least one olefinic compound to be oligomerised with the diluted activated catalyst of B to produce an oligomeric product.

20 Claims, 4 Drawing Sheets

Experimental apparatus used in examples 7-9

U.S. PATENT DOCUMENTS

2005/0020788 A1* 1/2005 Wass .................. 526/124.3
2005/0187098 A1* 8/2005 Knudsen et al. ............ 502/103

OTHER PUBLICATIONS

A. Carter et al., "High activity ethylene trimerisation catalysts based on diphosphine ligands", Chemical Communications—Chemcom, Royal Society of Chemistry, vol. 2002, No. 8, pp. 858-859 (2002).

D. McGuinness, "A Process for the Trimerisation and Tetramerisation of ethylene to 1-hexene and 1-Octene", IP.com electronic publication No. IPCOM000031729D, 11 pages (2004).

* cited by examiner

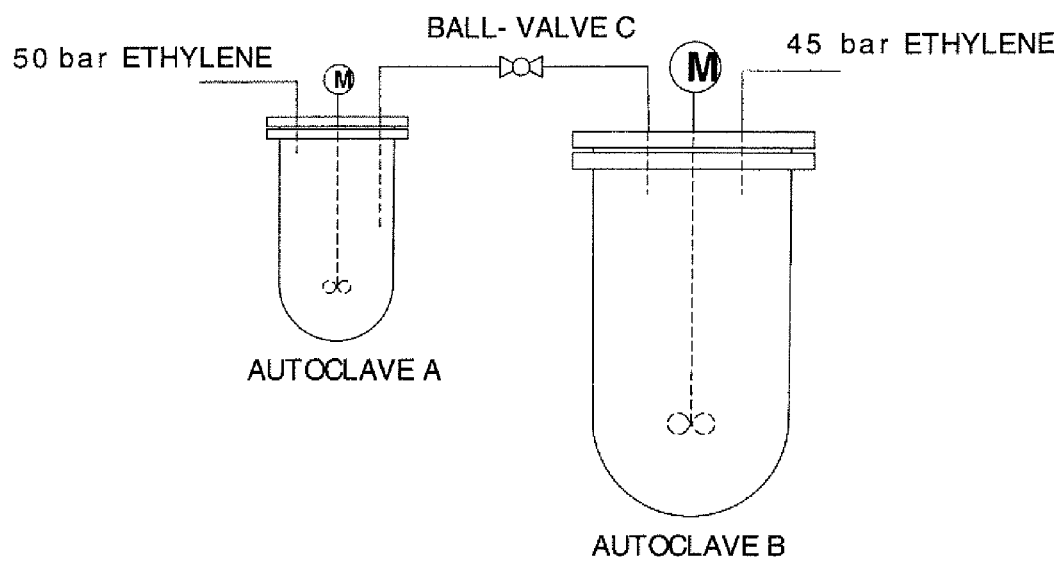
Figure 1: Experimental apparatus used in examples 7-9

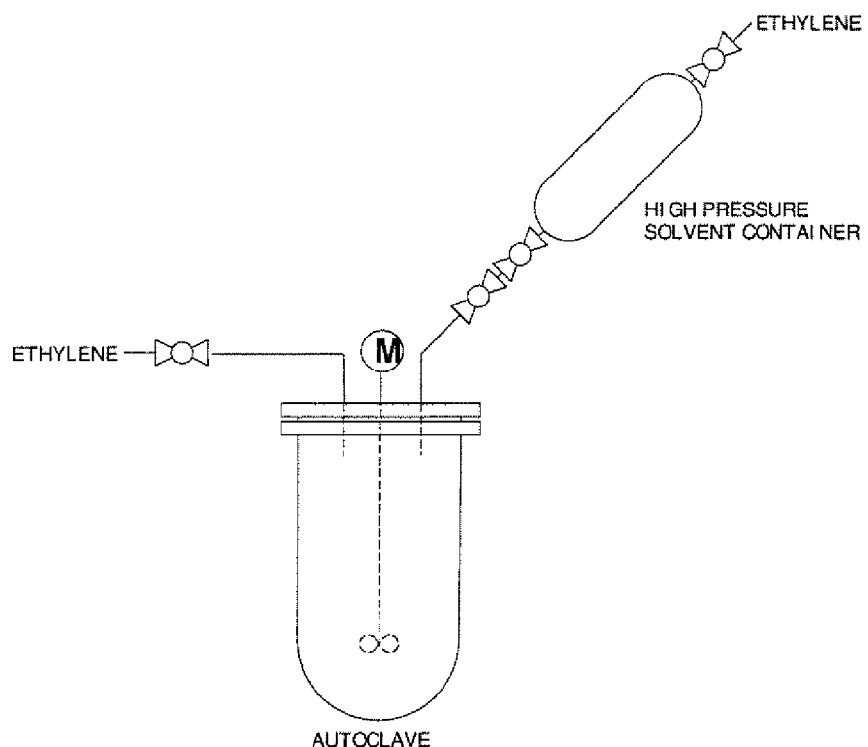
Figure 2: Apparatus for catalyst dilution examples 14, 19 and 24

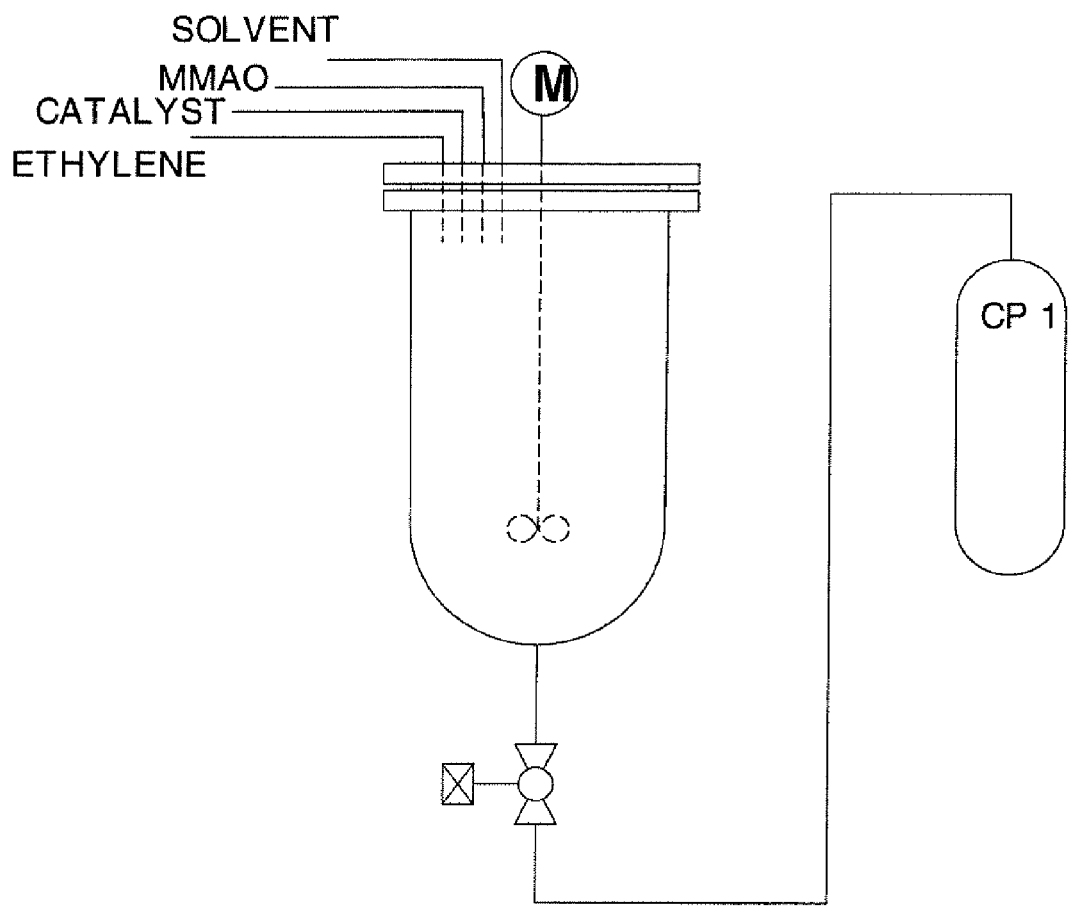
Figure 3: Apparatus used in comparative examples 25-28

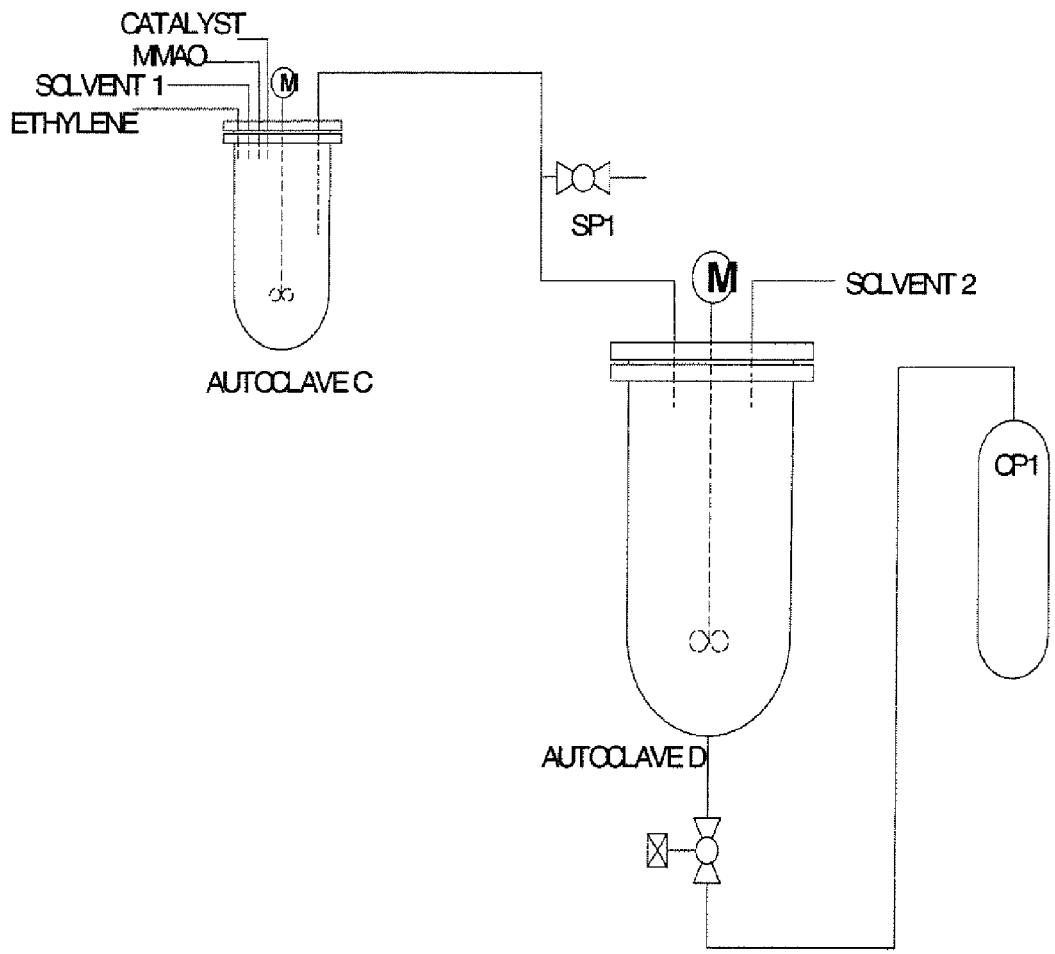
Figure 4: Apparatus used in example 29.

OLIGOMERISATION OF OLEFINIC COMPOUNDS IN THE PRESENCE OF A DILUTED METAL CONTAINING ACTIVATOR

TECHNICAL FIELD

This invention relates to the oligomerisation of olefinic compounds in the presence of a diluted oligomerisation catalyst activated by a metal containing activator.

BACKGROUND ART

A number of different oligomerisation technologies are known to produce α-olefins. Some of these processes, including the Shell Higher Olefins Process and Ziegler-type technologies, have been summarized in WO 04/056479 A1. The same document also discloses that the prior art (e.g. WO 03/053891 and WO 02/04119) teaches that chromium based catalysts containing heteroaromatic ligands with both phosphorus and nitrogen heteroatoms, selectively catalyse the trimerisation of ethylene to 1-hexene.

Processes wherein transition metals and heteroaromatic ligands are combined to form catalysts for trimerisation, tetramerisation, oligomerisation and polymerisation of olefinic compounds have also been described in different patent applications such as WO 03/053890 A1; WO 03/053891; WO 04/056479 A1; WO 04/056477 A1; WO 04/056480 A1; WO 04/056478 A1; WO 05/123884 A2; WO 05/123633 A1 and U.S. Complete patent application Ser. No. 11/130,106.

The catalysts utilized in the abovementioned trimerisation, tetramerisation, oligomerisation or polymerisation processes all include one or more activators to activate the catalyst. Such an activator is a compound that generates an active catalyst when the activator is combined with the catalyst.

Suitable activators include organoaluminium compounds, organoboron compounds, organic salts, such as methyl lithium and methyl magnesium bromide, inorganic acids and salts, such as tetrafluoroboric acid etherate, silver tetrafluoroborate, sodium hexafluoroantimonate and the like.

It is desirable to run a commercial oligomerisation process (e.g. ethylene tetramerisation) at low activator concentrations, especially where the activator is an aluminium containing compound, because the activators (especially aluminium containing compounds) are expensive.

However, in the case where an aluminium containing compound was used as an activator for transition metal based oligomerisation catalysts, it was found that at conditions of low starting aluminium concentrations (e.g. <6 mmol/l), low reaction rates and high levels of unwanted solids formation resulted when ethylene was oligomerised. This presented a major hurdle, since low final aluminium concentrations during catalysis is required and desirable for successful commercial operation.

SUMMARY OF INVENTION

In addition, the applicant has found that greater dilution of the catalyst with an introduced liquid medium after activation, increases the ratio of olefinic compound (e.g. ethylene) to primary reaction products (e.g. hexene or octene) in the reaction mixture, thus reducing the formation of secondary products (olefins of carbon number C10 or higher).

WO 02/04119 (e.g. in example 10) discloses preparation of a catalyst by combining a source of chromium with a ligand in a solvent. The solvent was then removed, the solid reaction product was suspended in toluene, and MAO was then added at a concentration of about 600 mmol/l. The subsequent solution was then injected into an autoclave containing a diluent in the form of isobutene, and ethylene trimerisation commenced at 8 bar ethylene pressure and 50° C.

It will be appreciated that in the above case of WO 02/04119, as well as the other prior art cases referred to above, no dilution of the activated catalyst by an introduced liquid medium took place after the catalyst was activated by the activator in the presence of an olefinic compound. As illustrated by the comparative examples of the present invention, activation of the catalyst by the activator in the presence of an olefinic compound prior to dilution can have a marked improvement in respect of reduced solids formation while retaining acceptable reaction rates or possibly even improving them.

BRIEF DESCRIPTION OF THE DRAWINGS

FIG. 1 shows the apparatus used in Examples 7-9,
FIG. 2 shows the apparatus used for catalyst dilution in Examples 14, 19 and 24.
FIG. 3 shows the apparatus used in Comparative Examples 25-28.
FIG. 4 shows the apparatus used in Example 29.

DISCLOSURE OF THE INVENTION

According to the present invention there is provided a process for producing an oligomeric product by the oligomerisation of at least one olefinic compound to be oligomerised, the at least one olefinic compound being in the form of an olefin or a compound including a carbon to carbon double bond, the process including:
A) providing an activated oligomerisation catalyst comprising the combination of
  i) a source of a transition metal;
  ii) a ligating compound of the formula

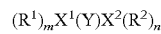

wherein: $X^1$ and $X^2$ are independently selected from the group consisting of N, P, As, Sb, Bi, O, S and Se;
    Y is a linking group between $X^1$ and $X^2$;
    m and n are independently 0, 1 or a larger integer; and
    $R^1$ and $R^2$ are independently hydrogen, a hydrocarbyl group or a heterohydrocarbyl group, and $R^1$ being the same or different when m>1, and $R^2$ being the same or different when n>1;
  iii) a metal containing activator; and
  iv) at least one olefinic compound in the form of an olefin or a compound including a carbon to carbon double bond;
  wherein components i) to iv), or one or more combinations thereof, have been combined in any suitable order to provide the activated oligomerisation catalyst;
B) diluting the activated oligomerisation catalyst of A with an introduced liquid medium, that is a liquid medium that has not been formed in situ by the process for producing an oligomeric product; and
C) contacting the at least one olefinic compound to be oligomerised with the diluted activated catalyst of B to produce an oligomeric product.

In this specification a hydrocarbyl group is a univalent or multivalent group formed by removing one or more hydrogen atoms from a hydrocarbon.

In this specification a heterohydrocarbyl group is a univalent or multivalent organic compound which includes at least one heteroatom (that is not being H or C), and which organic compound binds with one or more other moieties through one or more carbon atoms of the organic compound and/or one or more heteroatoms of the organic compound. Organoheteryl groups and organyl groups (which includes at least one heteroatom) are examples of heterohydrocarbyl groups.

According to another aspect of the present invention there is provided the use of an activated oligomerisation catalyst in the oligomerisation of at least one olefinic compound to be oligomerised, the olefinic compound being in the form of an olefin or a compound including a carbon to carbon double bond, the activated oligomerisation catalyst comprising the combination of
  i) a source of a transition metal;
  ii) a ligating compound of the formula

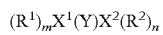
  $(R^1)_m X^1 (Y) X^2 (R^2)_n$ wherein: $X^1$ and $X^2$ are independently selected from the group consisting of N, P, As, Sb, Bi, O, S and Se;
    Y is a linking group between $X^1$ and $X^2$;
    m and n are independently 0, 1 or a larger integer; and
    $R^1$ and $R^2$ are independently hydrogen, a hydrocarbyl group or a heterohydrocarbyl group, and $R^1$ being the same or different when m>1, and $R^2$ being the same or different when n>1;
  (iii) a metal containing activator; and
  (iv) at least one olefinic compound in the form of an olefin or a compound including a carbon to carbon double bond;
  wherein components i) to iv), or one or more combinations thereof, have been combined in any suitable order to provide the activated oligomerisation catalyst; and
  the oligomerisation comprising diluting the activated oligomerisation catalyst with an introduced liquid medium, that is a liquid medium that has not been formed in situ by the process for producing an oligomeric product; and contacting the at least one olefinic compound to be oligomerised with the diluted activated oligomerisation catalyst to produce an oligomeric product.

Most surprisingly it has been found that under the conditions stated above, the oligomerisation does not result in unacceptable high polymerisation products such solids formation despite low concentrations of the metal of the metal containing activator after dilution of the activated catalyst, even where such concentrations are below 6 mmol/l. Such solids formation may be below 5 mass %, preferably below 2.5 mass %; and more preferably below 1 mass % where ethylene is the olefinic compound to be oligomerised.

It was also most surprisingly found that under such conditions the catalyst activity was acceptably high preferably above 50 000 g/g M/h, preferably above 100 000 g/g M/h and more preferably above 500 000 g/g M/h where M is the transition metal (preferably Cr) of the source of transition metal in the activated oligomerisation catalyst.

Activation

The metal containing activator may be a compound that generates an active catalyst when the activator is combined with the source of the transition metal, the ligating compound and the olefinic compound.

Preferably the activator is an aluminium containing compound such as an organoaluminium compound.

Suitable aluminium containing compounds include compounds of the formula $Al(R^9)_3$ ($R^9$ being the same or different), where each $R^9$ is independently a $C_1$-$C_{12}$ alkyl, an oxygen containing moiety or a halide; aluminoxanes; and compounds such as $LiAlH_4$ and the like. Aluminoxanes are well known in the art as typically oligomeric compounds which can be prepared by the controlled addition of water to an alkylaluminium compound, for example trimethylaluminium. In addition, there also exist non-hydrolytic routes for the preparation these compounds, Aluminoxanes can be linear, cyclic, cages or mixtures thereof. Examples of suitable aluminium containing compounds in the form of organoaluminium activators include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), isobutylaluminoxane (iBuAO), modified alkylaluminoxanes such as modified methylaluminoxane (MMAO) and mixtures thereof.

The activator may be selected from an alkylaluminoxane, including methylaluminoxane (MAO), high stability methylaluminoxane (MAO HS), ethylaluminoxane (EAO), isobutylaluminoxane (iBuAO); and modified alkylaluminoxane including modified methylaluminoxane (MMAO).

MMAO is methyl aluminoxane wherein one or more, but not all methyl groups have been replaced by one or more non-methyl moieties. Preferably the non-methyl moiety is an organyl, preferably a hydrocarbyl or a heterohydrocarbyl. Preferably it is an alkyl, preferably isobutyl or n-octyl.

The transition metal source (especially a source of chromium) and the aluminoxane may be combined in proportions to provide Al/transition metal molar ratios from about 1:1 to 10 000:1, preferably from about 1:1 to 5000:1, and more preferably from 300:1 to 4000:1; more preferably 300:1 to 900:1.

The process may include the step of adding to the catalyst system a trialkylaluminium compound in amounts of between 0.01 to 1000 mol per mol of alkylaluminoxane.

It should be noted that aluminoxanes generally also contain considerable quantities of the corresponding trialkylaluminium compounds used in their preparation. The presence of these trialkylaluminium compounds in aluminoxanes can be attributed to their incomplete conversion during the preparation of aluminoxanes. Any quantity of a trialkylaluminium compound quoted in this disclosure is additional to alkylaluminium compounds contained within the aluminoxanes.

Preferably the concentration of the metal (especially aluminium) of the metal containing activator in the activated catalyst prior to dilution is at least 3 mmol/l, preferably at least 6 mmol/l, preferably at least 9 mmol/l, preferably at least 12 mmol/l and even as high as 24 mmol/l or even higher. This is especially the case where aluminium is the metal in said metal containing activator in which case it is the concentration of the aluminium which is as stated above.

Oligomeric Product

The oligomeric product may be an olefin, or a compound including an olefinic moiety. Preferably the oligomeric product includes an olefin, more preferably an olefin containing a single carbon-carbon double bond, and preferably it includes an α-olefin. The olefin product may include hexene, preferably 1-hexene, but more preferably it includes octene, preferably 1-octene. In a preferred embodiment of the invention the olefinic product includes a mixture of hexene and octene, preferably a mixture of 1-hexene and 1-octene.

In one preferred embodiment of the invention the oligomerisation process is a selective process to produce an oligomeric product containing more than 30% by mass of a single olefin product. The olefin product may be hexene, preferably 1-hexene, but alternatively it may be octene, preferably 1-octene.

Preferably the product contains at least 35% of the said olefin, preferably α-olefin, but it may be more than 40%, 50%, or even 60% by mass.

The olefinic product may be branched, but preferably it is non-branched.

Oligomerisation

The oligomerisation process may comprise a trimerisation process, alternatively or additionally it may comprise a tetramerisation process.

The process may be oligomerisation of two or more different olefinic compounds to produce an oligomer containing the reaction product of the two or more different olefinic compounds. Preferably however, the oligomerisation (preferably trimerisation and/or tetramerisation) comprises the oligomerisation of a single monomer olefinic compound.

In one preferred embodiment of the invention the oligomerisation process is oligomerisation of a single α-olefin to produce an oligomeric α-olefin. Preferably it comprises the trimerisation and/or tetramerisation of ethylene, preferably to 1-hexene and/or 1-octene.

Olefinic Compound to be Oligomerised

The olefinic compound may comprise a single olefinic compound or a mixture of olefinic compounds. In one embodiment of the invention it may comprise a single olefin.

The olefin may include multiple carbon-carbon double bonds, but preferably it comprises a single carbon-carbon double bond. The olefin may comprise an α-olefin with 2 to 30 carbon atoms, preferably 2 to 10 carbon atoms. The olefinic compound may be selected from the group consisting of ethylene, propene, 1-butene, 1-pentene, 1-hexene, 1-heptene, and 1-octene, 1-nonene, 1-decene, 3-methyl-1-butene, 3-methyl-1-pentene, 4-methyl-1-pentene, styrene, p-methyl styrene, 1-dodecene or combinations thereof. Preferably it comprises ethylene or propene, preferably ethylene. The ethylene may be used to produce hexene and/or octene, preferably 1-hexene and/or 1-octene.

Source of Transition Metal

Preferably the source of transition metal is a source of a Group IV to VI transition metal. Preferably it is a source of Cr, Ti, V, Ta or Zr. Preferably it is a source of either Cr, Ta or Ti. Most preferably it is a source of Cr.

The source of the Group IV to VI transition metal may be an inorganic salt, an organic salt, a coordination compound or an organometallic complex.

Preferably the source of transition metal is a source of chromium and preferably it is selected from the group consisting of chromium trichloride tris-tetrahydrofuran complex; (benzene)tricarbonyl chromium; chromium (III) octanoate; chromium hexacarbonyl; chromium (III) acetylacetonate, chromium (III) naphthenate, chromium 2-ethylhexanoate. Preferably it is chromium (III) acetylacetonate.

Ligating Compound $X^1$ and/or $X^2$ may be a potential electron donor for coordination with the transition metal.

An electron donor is defined as an entity that donates electrons used in chemical, including dative covalent, bond formation.

$X^1$ and/or $X^2$, may be independently oxidised by S, Se, N or O.

$X^1$ and/or $X^2$ may be independently phosphorus or phosphorus oxidised by S or Se or N or O. Preferably $X^1$ and $X^2$ are the same, and preferably both are P.

It will be appreciated that m and n are dependent on factors such as the valence and oxidation state of $X^1$ and $X^2$, bond formation of Y with $X^1$ and $X^2$ respectively, and bond formation of $R^1$ and $R^2$ with $X^1$ and $X^2$ respectively. Preferably both m an n are not 0.

Preferably the ligating compound is a bidentate ligand.
Preferably the ligating compound is of the formula

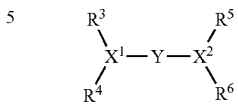

wherein Y is as defined above; $X^1$ and $X^2$ are independently selected from the group consisting of N, P, As, Sb and Bi; and $R^3$ to $R^6$ are each independently a hydrocarbyl group or a heterohydrocarbyl group.

Preferably $X^1$ and $X^2$ are independently selected from the group consisting of P and N. Preferably $X^1$ and $X^2$ are the same. Preferably both $X^1$ and $X^2$ are P.

One or more of $R^3$ to $R^6$ may be a substituted hydrocarbyl group or a substituted heterohydrocarbyl group, that is at least one substituent is bound to a hydrocarbyl group or a heterohydrocarbyl group.

In this specification a substituent with reference to compounds bound to $X^1$ and/or $X^2$ is a moiety (excluding H) which is bound to a linear structure or a cyclic structure bound to $X^1$ and/or $X^2$, but the substituent does not form part of the linear or cyclic structure.

The linear or cyclic structure may be selected from the group consisting of a linear hydrocarbyl, a linear heterohydrocarbyl a cyclic hydrocarbyl and a cyclic heterohydrocarbyl group. Linear hydrocarbyl may include methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, ethynyl, propynyl, butynyl, pentynyl, hexynyl, heptynyl, octynyl, nonynyl and decynyl.

Linear heterohydrocarbyl may include methoxy, ethoxy, thiomethoxy, thioethoxy, methylsilyl, ethylsilyl, methylamino, methylphosphino, methoxymethyl and thiomethoxymethyl. Cyclic hydrocarbyl may include cyclopropyl, cyclobutyl, cyclopentyl, cyclohexyl, cycloheptyl, cyclooctyl, cyclononyl, cyclodecyl, cyclopentenyl, cyclohexenyl, cyclo-octenyl, phenyl, cyclopentadienyl, naphthaleneyl, norbornyl, adamantyl, phenanthreneyl, anthraceneyl, phenaleneyl, tetrahydronaphthaleneyl, decalinyl, indenyl and tetrahydroindenyl. Cyclic heterohydrocarbyl may include tetrahydrofuranyl, tetrahydrothiopheneyl, pyrrolideneyl, piperidineyl, pyrrolineyl, oxazolyl, thiazolyl, furanyl, thiopheneyl, pyrazolinyl, pyrazolyl, imidazolyl, benzofuranyl, coumaranyl and indolyl.

According to the above definition and for the purpose of clarity, benzyl is considered as a methyl single carbon atom containing structure with a phenyl substituent and tolyl is considered to be a phenyl cyclic structure with a methyl substituent.

$R^3$ to $R^6$ may also be selected from a group of metallocenes such as a ferroceneyl, zirconoceneyl and titanoceneyl group.

Preferably none of $R^3$ to $R^6$ are aromatic with a ring atom of the aromatic ring structure bound to either $X^1$ or $X^2$ and with a polar substituent as a non-ring atom bound to a ring atom of the aromatic ring structure adjacent to the ring atom bound to $X^1$ or $X^2$.

In this specification a polar substituent is a substituent with a permanent electric or induced dipole moment.

Preferably, if two or more of $R^3$ to $R^6$ are aromatic with a ring atom of the aromatic ring structure bound to either $X^1$ and $X^2$ not more than two of said aromatic $R^3$ and $R^6$ have a substituent as a non-ring atom bound to a ring atom of the aromatic ring structure adjacent to the ring atom bound to $X^1$ or $X^2$.

In one embodiment of the invention $R^3$ to $R^6$ are the same or different and each is a hydrocarbyl group, or a heterohydrocarbyl group (preferably an organyl group) which contains no substituent or contains a non-polar substituent. Preferably each of $R^3$ to $R^6$ does not include any polar substituent. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a non-polar substituent other than H as a non-ring atom bound to a ring atom of the aromatic ring structure adjacent to the ring atom bound to $X^1$ or $X^2$.

Preferably none of the aromatic $R^3$ to $R^6$ have a non-polar substituent as a non-ring atom bound to a ring atom of the aromatic ring structure adjacent to the ring atom bound to $X^1$ or $X^2$. Preferably all of aromatic $R^3$ to $R^6$ are non-substituted aromatic compounds. $R^3$ to $R^6$ may be independently selected from the group consisting of a non-aromatic compound; an aromatic compound; and a heteroaromatic compound. Preferably each of $R^3$ to $R^6$ is an aromatic or heteroaromatic compound, more preferably an aromatic compound (including a substituted aromatic compound). The aromatic compound (or substituted aromatic compound) may comprise phenyl or a substituted phenyl.

In this specification a non-polar substituent is a substituent without a permanent electric or induced dipole moment.

Examples of suitable non-polar substituents include, but are not limited to, methyl, ethyl, ethenyl, propyl, iso-propyl, cyclopropyl, propenyl, propynyl, butyl, sec-butyl, tertiary-butyl, cyclobutyl, butenyl, butynyl, pentyl, isopentyl, neopentyl, cyclopentyl, pentenyl, pentynyl, hexyl, sec-hexyl, cyclohexyl, 2-methylcyclohexyl, 2-ethylcyclohexyl, 2-isopropylcyclohexyl, cyclohexenyl, hexynyl, hexynyl, octyl, cyclo-octyl, cyclo-octenyl, decyl, benzyl, phenyl, tolyl, xylyl, o-methylphenyl, o-ethylphenyl, o-isopropylphenyl, o-t-butylphenyl, cumyl, mesityl, biphenyl, naphthyl, anthracenyl, and the like.

Any one of $R^3$ to $R^6$ may be independently linked to one or more of each other, or to Y to form a cyclic structure.

$R^3$ and $R^4$ may be the same and $R^6$ and $R^6$ may be the same. $R^3$ to $R^6$ may all be the same.

In another embodiment of the invention $R^3$ to $R^6$ are the same or different and each is a hydrocarbyl group, or a heterohydrocarbyl group (preferably an organyl group), provided that at least one of $R^3$ to $R^6$ contains a polar substituent on a carbon atom, but not one of $R^3$ to $R^6$ contains a polar substituent on a carbon atom of $R^3$ to $R^6$ adjacent to a carbon atom bound to $X^1$ or $X^2$. One or more or all of $R^3$ to $R^6$ may be independently selected from the group consisting of a substituted non-aromatic compound; a substituted aromatic compound; and a substituted heteroaromatic compound. Preferably each of $R^3$ to $R^6$ is a substituted aromatic or a substituted heteroaromatic compound, more preferably a substituted aromatic compound. The substituted aromatic compound may comprise a substituted phenyl. In one embodiment of the invention at least two of (but preferably all of) $R^3$ to $R^6$ are aromatic with a ring atom of the aromatic ring structure bound to $X^1$ or $X^2$, but preferably not more than two of said aromatic $R^3$ to $R^6$ have a substituent as a non-ring atom bound to a ring atom of the aromatic ring structure adjacent to the ring atom bound to $X^1$ or $X^2$.

Any polar substituent on one or more of $R^3$, $R^4$, $R^6$ and $R^6$ may be electron donating.

Suitable polar substituents may be a methoxy, ethoxy, isopropoxy, $C_3$-$C_{20}$ alkoxy, phenoxy, methoxymethyl, methylthiomethyl, 1,3-oxazolyl, methoxymethoxy, hydroxyl, amino, pentafluorophenoxy, tosyl, methylsulfanyl, trimethylsiloxy, dimethylamino, sulphate, nitro, halides or the like.

Y may be selected from the group consisting of an organic linking group such as a hydrocarbyl, substituted hydrocarbyl, heterohydrocarbyl and a substituted heterohydrocarbyl; an inorganic linking group such as a single atom link (that is $X^1$ and $X^2$ are bound to the same atom); methylene; dimethylmethylene; 1,2-ethane; 1,2-ethene; 1,1-cyclopropane; 1,1-cyclobutane; 1,1-cyclohexane; 1,1-cyclopentane; 1,2-cyclopentane; 1,2-cyclohexane; 1,2-phenylene; 1,8-naphthyl; 9,10-phenanthrene; 4,5-phenanthrene; 1,3-propane; 1,2-catechol, 1,2-diarylhydrazine and 1,2-dialkylhydrazine; —B($R^7$)—, —Si($R^7$)$_2$—, —P($R^7$)— and —N($R^7$)— where $R^7$ is hydrogen, a hydrocarbyl or heterocarbyl or inorganic group including halogen. Preferably, Y may be —N($R^7$)— and $R^7$ may be selected from the group consisting of hydrogen, alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. Preferably $R^7$ may be a hydrocarbyl or a heterohydrocarbyl group. $R^7$ may be methyl, ethyl, propyl, isopropyl, cyclopropyl, allyl, butyl, tertiary-butyl, sec-butyl, cyclobutyl, pentyl, isopentyl, neopentyl, cyclopentyl, cyclohexyl, cycloheptyl, cyclo-octyl, decyl, cyclodecyl, 1,5-dimetylheptyl, 2-naphthylethyl, 1-naphthylmethyl, adamantylmethyl, adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, isopinocamphenyl, dimethylamino, phthalimido, pyrrolyl, trimethylsilyl, dimethyl-tertiary-butylsilyl, 3-trimethoxylsilane-propyl, indanyl, cyclohexanemethyl, 2-methoxyphenyl, 3-methoxyphenyl, 4-methoxyphenyl, 4-tertiary-butylphenyl, 4-nitrophenyl, (1,1'-bis(cyclohexyl)-4,4'-methylene), 1,6-hexylene, 1-naphthyl, 2-naphthyl, N-morpholine, diphenylmethyl, 1,2-diphenyl-ethyl, phenylethyl, 2-methylphenyl, 3-methylphenyl, 4-methylphenyl, 2,6-dimethyl-phenyl, 1,2,3,4-tetrahydronaphthyl, or a 2-octyl group.

Y may exclude $(CH_2)_xZ(CH_2)_y$, where Z is —P($R^8$)—, —N($R^8$)—, —As($R^8$)—, —Sb($R^8$)— or —S— and x and y are individually 1-15 and wherein $R^8$ is hydrogen or a halogen or a nitro group or a hydrocarbyl or a substituted hydrocarbyl group.

Y may include a first atom bound to $X^1$ and a different atom bound to $X^2$, such as the case where Y is 1,2 ethane. Preferably Y includes or is a single atom bound to both $X^1$ and $X^2$.

Preferably the ligating compound is of the formula

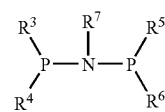

with $R^3$ to $R^7$ as defined above.

Preferably each of $R^3$ to $R^6$ is an alkyl (preferably methyl, ethyl or isopropyl) or aromatic (preferably phenyl or substituted phenyl).

The ligating compound may include a polymeric moiety to render the reaction product of the source of transition metal and the said ligating compound to be soluble at higher temperatures and insoluble at lower temperatures e.g. 25° C. This approach may enable the recovery of the complex from the reaction mixture for re-use and has been used for other catalyst as described by D. E. Bergbreiter et al., *J. Am. Chem. Soc.*, 1987, 109, 177-179. In a similar vein these transition metal catalysts can also be immobilised by binding the ligating compound to silica, silica gel, polysiloxane or alumina backbone as, for example, demonstrated by C. Yuanyin et al., *Chinese J. React. Pol.*, 1992, 1(2), 152-159 for immobilising platinum complexes.

The ligating compound may include multiple ligating units or derivatives thereof. Non-limiting examples of such ligands include dendrimeric ligands as well as ligands where the individual ligating units are coupled either via one or more of the R groups or via the linking group Y. More specific, but not limiting, examples of such ligands may include 1,2-di-(N(P (phenyl)$_2$)$_2$)-benzene, 1,4-di-(N(P(phenyl)$_2$)$_2$)-benzene, N(CH$_2$CH$_2$N(P(phenyl)$_2$)$_2$)$_3$, 1,4-di-(P(phenyl)N(methyl)P (phenyl)$_2$)-benzene, 1,2-di-(N(P(p-methoxyphenyl)$_2$)$_2$)-benzene, 1,4-di-(N(P(p-methoxyphenyl)$_2$)$_2$)-benzene, N(CH$_2$CH$_2$N(P(p-methoxyphenyl)$_2$)$_2$)$_3$ and 1,4-di-(P(p-methoxyphenyl)N(methyl)P(p-methoxyphenyl)$_2$)-benzene.

The ligating compounds may be prepared using procedures known to one skilled in the art and procedures forming part of the state of the art.

Catalyst Preparation

The process may include the step of preparing the activated catalyst.

It is foreseen that i) the source of the transition metal and ii) the said ligating compound (e.g. referred to in A) may be first reacted together and the resulting product may even be isolated, before combining it with the metal containing activator iii). However, i), ii) and iii) may be combined in any suitable order in the presence of the olefinic compound iv), but preferably at least some, but preferably all of i), ii) and iii) are first combined and subsequently contacted with the olefinic compound iv).

The olefinic compound referred to in iv) is preferably the same as the olefinic compound to be oligomerised.

The contacting of the olefinic compound Iv) with compounds i) to iii) preferably takes place under conditions to allow oligomerisation of the olefinic compound iv). These conditions are well known to a person skilled in the art and include elevated temperatures and pressure. Preferably it is carried out at a temperature of at least 0° C., preferably at least 40° C., and preferably at least 50° C. Preferably it is carried out at a pressure of at least 100 kPa, preferably at least 1000 kPa, preferably at least 3000 kPa.

The preparation of the activated catalyst may be carried out in a liquid medium, preferably an inert liquid medium. The liquid medium may be the same liquid medium wherein the oligomerisation with the diluted catalyst is carried out.

The activated oligomerisation catalyst before dilution may be prepared in the same container as the one in which the diluted activated oligomerisation catalyst is contacted with the olefinic compound to be oligomerised. Preferably the activated oligomerisation catalyst before dilution is prepared in a separate container as the one in which the oligomerisation catalyst is contacted with the olefinic compound to be oligomerised.

The source of transition metal (preferably chromium) and ligating compound may be combined to provide any suitable molar ratio, preferably a transition metal to ligand compound molar ratio, from about 0.01:100 to 10 000:1, preferably from about 0.1:1 to 10:1.

The process may also include combining one or more different sources of transition metal with one or more different ligating compounds.

The oligomerisation catalyst or its individual components, in accordance with the invention, may also be immobilised by supporting it on a support material, for example, silica, alumina, MgCl$_2$, zirconia, artificial hectorite or smectorite clays such as Laponite™ RD or mixtures thereof, or on a polymer, for example polyethylene, polypropylene, polystyrene, or poly(aminostyrene). The catalyst can be formed in situ in the presence of the support material, or the support can be pre-impregnated or premixed, simultaneously or sequentially, with one or more of the catalyst components or the oligomerisation catalyst. In some cases, the support material can also act as a component of the activator. This approach would also facilitate the recovery of the catalyst from the reaction mixture for reuse.

Dilution of the Activated Catalyst

As stated above the activated catalyst is diluted with an introduced liquid medium, preferably in order to reduce the concentration of the metal (preferably aluminium) of the metal containing activator before contacting the activated catalyst with the olefinic compound to be oligomerised.

The introduced liquid medium may be the same as an oligomerisation product produced by the process, except that it is introduced from an external source. Accordingly the introduced liquid medium may be an olefinic moiety.

Preferably the introduced liquid medium is different from the said oligomerisation product and preferably it is an inert liquid medium. The introduced liquid medium may be the same as a liquid medium wherein the oligomerisation with the diluted activated catalyst is carried out and which liquid medium is as described later in this specification.

After dilution of the activated catalyst with the introduced liquid medium the concentration of the metal (preferably Al) of the metal containing activator is preferably not above 12 mmol/l, and preferably it is below 9 mmol/l. Preferably it is below 6 mmol/l and more preferably it is not above 3 mmol/l.

Oligomerisation with the Diluted Activated Catalyst

The oligomerisation with the diluted activated catalyst may be carried out at a pressure of above 1 bar, preferably above 10 bar, more preferably above 40 bar, preferably at 50 bar or even higher. Preferred pressure ranges are from 10 to 300 bar, more preferably from 30 to 100 bar.

The said oligomerisation may be carried out at temperatures from −100 to 250° C., but temperatures in the range of 15 to 130° C. are preferred. Particularly preferred temperatures range from 50 to 120° C.

The said oligomerisation may be carried out in a liquid medium. Preferably the liquid medium is an inert liquid medium. The liquid medium may be aromatic (including heteroaromatic) or aliphatic. Preferably the liquid medium comprises an aliphatic medium and the aliphatic liquid medium may comprise an acyclic compound or mixtures thereof, but preferably it comprises a cyclic compound or alkyl substituted derivatives thereof. The cyclic compound may include hetero-atoms (that is atoms other that H and C), but preferably comprises a cyclic hydrocarbon. The cyclic hydrocarbon may include one or more unsaturated carbon atoms, but preferably it is a saturated cyclic hydrocarbon. The ring structure of the saturated cyclic hydrocarbon may consist of 3 to 12 carbon atoms, preferably 5 to 8 carbon atoms. In one embodiment of the invention the ring structure of the saturated cyclic hydrocarbon may consist of 6 carbon atoms.

In one preferred embodiment of the invention the aliphatic liquid medium may comprise cyclohexane or methylcyclohexane. Last mentioned compound is especially suitable from a product separation/solvent recycle point of view in oligomerisation of ethylene.

It has been found that aliphatic liquid mediums such as cyclohexane provide more active reaction systems (compared to aromatic liquid mediums) which can reduce catalyst usage. Aliphatic liquid mediums are also more environmentally friendly than aromatic compounds.

In a preferred embodiment of the invention the liquid medium is a solvent for the olefinic compound and/or the oligomerisation catalyst, preferably of both.

The olefinic compound or mixture thereof to be oligomerised according to this invention can be introduced into the process in a continuous or batch fashion.

Preferably, the reaction conditions of the process are chosen such to produce oligomers (especially trimers and/or tetramers) in high yield by selectively converting an ethylenic feedstock such as ethylene.

The process may include a process for the oligomerisation (especially tri- or tetramerisation) of ethylene or propylene or a mixture of olefins to yield an oligomerised product selectively.

The reaction products derived from the oligomerisation reaction as described herein, may be prepared using the disclosed catalyst by a homogeneous liquid phase reaction in the presence or absence of an inert solvent, and/or by slurry reaction where the catalyst and the polymeric product is in a form that displays little or no solubility, and/or a two-phase liquid/liquid reaction, and/or a bulk phase reaction in which neat reagent and/or product olefins serve as the dominant medium, and/or gas phase reaction, using conventional equipment and contacting techniques.

The oligomerisation with the diluted activated catalyst may be carried out in a plant which includes reactor types known in the art. Examples of such reactors include, but are not limited to, batch reactors, semi-batch reactors and continuous reactors. The plant may include, in combination a) at least one reactor system, b) at least one inlet line into this reactor for olefin reactant and the catalyst system, c) effluent lines from this reactor for oligomerised reaction products, and d) at least one separator to separate the desired oligomerised reaction products, which may include a recycle loop for solvents and/or reactants and/or products which may also serve as a temperature control mechanism.

The invention also relates to an oligomeric product produced by the process substantially as described hereinabove.

The invention will now be further described by means of the following non-limiting examples.

EXAMPLES

The individual components of the examples may conceivably be omitted or substituted and, although not necessarily ideal, the invention may conceivably still be performed and these components are not to be taken as essential to the working of the invention.

In the examples that follow all procedures were carried out under inert conditions, using pre-dried reagents. Chemicals were obtained from Sigma-Aldrich or Strem Chemicals unless stated otherwise. All trialkylaluminium and aluminoxane compounds and solutions thereof were obtained from Crompton Gmbh, Akzo Nobel and Albemarle Corporation. In all the examples, the molar mass of methylaluminoxane (MAO and MAO-HS) was taken to be 58.016 g/mol, corresponding to the ($CH_3$—Al—O) unit, in order to calculate the molar quantities of MAO and MAO-HS used in the preparation of the catalysts described in the examples below. Similarly the molar mass of modified methylaluminoxane prepared from a 70:30 mixture of trimethylaluminium and tri-isobutylaluminium was taken as 70.7 g/mol corresponding to the ($Me_{0.70}isoBu_{0.30}$—Al—O) unit. Ethylene oligomerisation products were analysed by GC-MS and GC-FID.

The ligating compounds employed were prepared according to procedures disclosed in WO 2004/056479 and *J. Am. Chem. Soc.*, 2004, 126, 14712 and references cited therein.

Examples 1 to 6 are comparative batch run examples wherein no dilution of the activated catalyst (including the aluminium of the aluminium containing activator and an olefin) by means of an introduced liquid medium was done. After commencement of the oligomerisation reaction some dilution took place due to the formation of the liquid olefin oligomerisation product itself, but this is not dilution by means of a introduced liquid medium as described in this specification. The aluminium concentration ([Al]) during catalyst activation in the presence of an olefin and a significant part of the oligomerisation itself were consequently relatively similar.

Examples 7 and 8 are according to the invention, that is activation in the presence of an olefin of the catalyst took place at a relatively high [Al] and oligomerisation after dilution of the activated catalyst took place at a relatively low [Al].

Examples 9 is a further example wherein the procedure of examples 7 and 8 was followed, but the [Al] was substantially the same during activation of the catalyst in the presence of an olefin and during oligomerisation with the diluted activated catalyst.

Comparative Example 1

An inertised 1 liter autoclave was charged with methylcyclohexane (195 ml) and pressurised to 40 bar (4000 kPa) ethylene. In a Schlenk tube, a mixture of $Cr(acac)_3$ (5.0 μmol) and $Ph_2PN(iPr)PPh_2$ (5.0 μmol) in methylcyclohexane (5 ml) was treated with MMAO-3A (2.395 mmol Al). After stirring for one minute, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 60° C. and 45 bar (4500 kPa). After 44 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 311 g. The solids were recovered by filtration and dried at 70° C. The mass was found to be 0.9 g. The selectivity and rates are shown in Table 1.

Comparative Example 2

An inertised 1 liter autoclave was charged with methylcyclohexane (195 ml) and pressurised to 40 bar (4000 kPa) ethylene. In a Schlenk tube, a mixture of $Cr(acac)_3$ (5.0 μmol) and $Ph_2PN(iPr)PPh_2$ (5.0 μmol) in methylcyclohexane (5 ml) was treated with MMAO-3A (2.395 mmol Al). After stirring for one minute, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 60° C. and 45 bar (4500 kPa). After 44 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 313 g. The solids were recovered by filtration and dried at 70° C. The mass was found to be 1.0 g. The selectivity and rates are shown in Table 1.

Comparative Example 3

An inertised 1 liter autoclave was charged with methylcyclohexane (195 ml) and pressurised to 40 bar (4000 kPa) ethylene. In a Schlenk tube, a mixture of $Cr(acac)_3$ (2.5 µmol) and $Ph_2PN(iPr)PPh_2$ (2.5 µmol) in methylcyclohexane (5 ml) was treated with MMAO-3A (1.198 mmol Al). After stirring for one minute, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 60° C. and 45 bar (4500 kPa). After 294 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 307 g. The solids were recovered by filtration and dried at 70° C. The mass was found to be 6.9 g. The selectivity and rates are shown in Table 1.

Comparative Example 4

An inertised 1 liter autoclave was charged with methylcyclohexane (195 ml) and pressurised to 40 bar (4000 kPa) ethylene. In a Schlenk tube, a mixture of $Cr(acac)_3$ (2.5 µmol) and $Ph_2PN(iPr)PPh_2$ (2.5 µmol) in methylcyclohexane (5 ml) was treated with MMAO-3A (2.395 mmol Al). After stirring for one minute, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 60° C. and 45 bar (4500 kPa). After 138 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 292 g. The solids were recovered by filtration and dried at 70° C. The mass was found to be 1.2 g. The selectivity and rates are shown in Table 1.

Comparative Example 5

An inertised 1 liter autoclave was charged with methylcyclohexane (195 ml) and pressurised to 40 bar (4000 kPa) ethylene. In a Schlenk tube, a mixture of $Cr(acac)_3$ (1.0 µmol) and $Ph_2PN(iPr)PPh_2$ (1.0 µmol) in methylcyclohexane (5 ml) was treated with MMAO-3A (0.479 mmol Al). After stirring for one minute, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 60° C. and 45 bar (4500 kPa). After 120 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 13.0 g. The solids were recovered by filtration and dried at 70° C. The mass was found to be 11.9 g. The selectivity and rates are shown in Table 1.

Comparative Example 6

An inertised 1 liter autoclave was charged with methylcyclohexane (195 ml) and pressurised to 40 bar (4000 kPa) ethylene. In a Schlenk tube, a mixture of $Cr(acac)_3$ (1.0 µmol) and $Ph_2PN(iPr)PPh_2$ (1.0 µmol) in methylcyclohexane (5 ml) was treated with MMAO-3A (2.395 mmol Al). After stirring for one minute, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 60° C. and 45 bar (4500 kPa). After 120 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 38.3 g. The solids were recovered by filtration and dried at 70° C. The mass was found to be 0.8 g. The selectivity and rates are shown in Table 1.

Apparatus for Examples 7-9

Two inertised autoclave reactors of volumes 300 ml (autoclave A) and 1 liter (autoclave B) and equipped with gas entraining stirrers were connected with a dip-tube from autoclave A as shown in FIG. 1. The connecting pipe was equipped with a ball-valve (ball-valve C) such that the autoclaves could be separated from each other. Autoclaves A and B were independently equipped with a supply of ethylene at 50 bar and 45 bar pressures respectively.

Example 7

Autoclave B was charged with methylcyclohexane (250 ml) and MMAO-3A (0.42 mmol Al). With ball-valve C closed, autoclave B was pressurised to 45 bar (4500 kPa) ethylene. Autoclave A was charged with methylcyclohexane (95 ml). In a Schlenk-tube, a mixture of $Cr(acac)_3$ (5.0 µmol), $Ph_2PN(iPr)PPh_2$ (5.0 µmol) in methylcyclohexane (5 ml) was treated with MMAO-3A (2.395 mmol Al). After stirring for one minute, this mixture was transferred to autoclave A which was sealed and pressurised to 50 bar (5000 kPa) with ethylene. The mixture was stirred at 1100 r.p.m. to ensure thorough mass transfer. The uptake of ethylene into autoclave A was monitored, and the temperature and pressure were maintained at 60° C. and 50 bar (5000 kPa). After 7 minutes, 58 g of ethylene uptake was recorded. Ball-valve C was opened for 5 seconds, thus forcing some of the reaction mixture from autoclave A into autoclave B. The uptake of ethylene into autoclave B was monitored, and the temperature and pressure of autoclave B were maintained at 60° C. and 45 bar (4500 kPa). The mixture was stirred at 1100 r.p.m. to ensure thorough mass transfer. After 35 minutes, the supply of ethylene was terminated and autoclave B was cooled to less than 15° C. and slowly depressurised. A known mass of nonane was added as an internal standard. A sample of the liquid fraction was filtered and analysed by GC-FID. The mass of ethylene oligomers (305 g) and methylcyclohexane was determined relative to this standard. From this, the amount of methylcyclohexane transferred to autoclave B was calculated (46 g), and hence the amount of Cr (3.0 mmol), Al (1.44 mmol) and oligomers (35 g) transferred. The mass of oligomers produced in autoclave B was thus determined to be 280 g. The solids were recovered by filtration and dried at 70° C. The mass was found to be 1.2. The selectivity and rates are shown in Table 1.

Example 8

Autoclave B was charged with methylcyclohexane (300 ml) and MMAO-3A (0.40 mmol Al). With ball-valve C closed, autoclave B was pressurised to 45 bar (4500 kPa) ethylene. Autoclave A was charged with methylcyclohexane (95 ml). In a Schlenk-tube, a mixture of Cr(acac)$_3$ (2.5 µmol), Ph$_2$PN(iPr)PPh$_2$ (2.5 µmol) in methylcyclohexane (5 ml) was treated with MMAO-3A (1.198 mmol Al). After stirring for one minute, this mixture was transferred to autoclave A which was sealed and pressurised to 50 bar (5000 kPa) with ethylene. The mixture was stirred at 1100 r.p.m. to ensure thorough mass transfer. The uptake of ethylene into autoclave A was monitored, and the temperature and pressure were maintained at 60° C. and 50 bar (5000 kPa). After 8 minutes, 47 g of ethylene uptake was recorded. Ball-valve C was opened for 3 seconds, thus forcing some of the reaction mixture from autoclave A into autoclave B. The uptake of ethylene into autoclave B was monitored, and the temperature and pressure of autoclave B were maintained at 60° C. and 45 bar (4500 kPa). The mixture was stirred at 1100 r.p.m. to ensure thorough mass transfer. After 120 minutes, the supply of ethylene was terminated and autoclave B was cooled to less than 15° C. and slowly depressurised. A known mass of nonane was added as an internal standard. A sample of the liquid fraction was filtered and analysed by GC-FID. The mass of ethylene oligomers (164 g) and methylcyclohexane was determined relative to this standard. From this, the amount of methylcyclohexane transferred to autoclave B was calculated (31 g), and hence the amount of Cr (1.0 mmol), Al (0.48 mmol) and oligomers (19 g) transferred. The mass of oligomers produced in autoclave B was thus determined to be 145 g. The solids were recovered by filtration and dried at 70° C. The mass was found to be 0.9 g. The selectivity and rates are shown in Table 1.

Example 9

Autoclave B was charged with methylcyclohexane (300 ml) and MMAO-3A (3.67 mmol Al). With ball-valve C closed, autoclave B was pressurised to 45 bar (4500 kPa) ethylene. Autoclave A was charged with methylcyclohexane (95 ml). In a Schlenk-tube, a mixture of Cr(acac)$_3$ (2.5 µmol), Ph$_2$PN(ipr)PPh$_2$ (2.5 µmol) in methylcyclohexane (5 ml) was treated with MMAO-3A (1.198 mmol Al). After stirring for one minute, this mixture was transferred to autoclave A which was sealed and pressurised to 50 bar (5000 kPa) with ethylene. The mixture was stirred at 1100 r.p.m. to ensure thorough mass transfer. The uptake of ethylene into autoclave A was monitored, and the temperature and pressure were maintained at 60° C. and 50 bar (5000 kPa). After 8 minutes, 47 g of ethylene uptake was recorded. Ball-valve C was opened for 3 seconds, thus forcing some of the reaction mixture from autoclave A into autoclave B. The uptake of ethylene into autoclave B was monitored, and the temperature and pressure of autoclave B were maintained at 60° C. and 45 bar (4500 kPa). The mixture was stirred at 1100 r.p.m. to ensure thorough mass transfer. After 120 minutes, the supply of ethylene was terminated and autoclave B was cooled to less than 15° C. and slowly depressurised. A known mass of nonane was added as an internal standard. A sample of the liquid fraction was filtered and analysed by GC-FID. The mass of ethylene oligomers (140 g) and methylcyclohexane was determined relative to this standard. From this, the amount of methylcyclohexane transferred to autoclave B was calculated (34 g), and hence the amount of Cr (1.1 mmol), Al (0.53 mmol) and oligomers (21 g) transferred. The mass of oligomers produced in autoclave B was thus determined to be 119 g. The solids were recovered by filtration and dried at 70° C. The mass was found to be 0.9 g. The selectivity and rates are shown in Table 1.

Comparative Example 10

An inertised 450 ml autoclave was charged with methylcyclohexane (98 ml). In a Schlenk tube, a mixture of Cr(acac)$_3$ (2.5 µmol) and (o-ethylphenyl)$_2$PN(Me)P(o-ethylphenyl)$_2$ (2.5 µmol) in methylcyclohexane was treated with MMAO-3A (2.4 mmol Al). After stirring for 30 seconds, this mixture was added to the autoclave which was then pressurised to 30 bar (3000 kPa) ethylene. The mixture was stirred at 1100 r.p.m. to ensure thorough mass transfer. The uptake of ethylene into the autoclave was monitored, and the temperature and pressure were maintained at 60° C. and 30 bar (3000 kPa). After 15 minutes, the supply of ethylene was terminated and the autoclave was cooled to less than 25° C. and slowly depressurised. A sample of the liquid fraction was filtered and analysed by GC-FID. The mass of ethylene oligomers was found to be 143.6 g. The solids were recovered by filtration and dried at 70° C. The mass was found to be 1.2 g. The selectivity and rates are shown in Table 1.

Comparative Example 11

An inertised 450 ml autoclave was charged with methylcyclohexane (99 ml). In a Schlenk tube, a mixture of Cr(acac)$_3$ (1.25 µmol) and (o-ethylphenyl)$_2$PN(Me)P(o-ethylphenyl)$_2$ (1.25 µmol) in methylcyclohexane was treated with MMAO-3A (1.2 mmol Al). After stirring for 30 seconds, this mixture was added to the autoclave which was then pressurised to 30 bar (3000 kPa) ethylene. The mixture was stirred at 1100 r.p.m. to ensure thorough mass transfer. The uptake of ethylene into the autoclave was monitored, and the temperature and pressure were maintained at 60° C. and 30 bar (3000 kPa). After 20 minutes, the supply of ethylene was terminated and the autoclave was cooled to less than 25° C. and slowly depressurised. A sample of the liquid fraction was filtered and analysed by GC-FID. The mass of ethylene oligomers was found to be 110.1 g. The solids were recovered by filtration and dried at 70° C. The mass was found to be 8.2 g. The selectivity and rates are shown in Table 1.

Comparative Example 12

An inertised 450 ml autoclave was charged with methylcyclohexane (98 ml). In a Schlenk tube, a mixture of Cr(acac)$_3$ (1.25 µmol) and (o-ethylphenyl)$_2$PN(Me)P(o-ethylphenyl)$_2$ (1.25 µmol) in methylcyclohexane was treated with MMAO-3A (2.4 mmol Al). After stirring for 30 seconds, this mixture was added to the autoclave which was then pressurised to 30 bar (3000 kPa) ethylene. The mixture was stirred at 1100 r.p.m. to ensure thorough mass transfer. The uptake of ethylene into the autoclave was monitored, and the temperature and pressure were maintained at 60° C. and 30 bar (3000 kPa). After 17.5 minutes, the supply of ethylene was terminated and the autoclave was cooled to less than 25° C. and slowly depressurised. A sample of the liquid fraction was filtered and analysed by GC-FID. The mass of ethylene oligomers was found to be 133.2 g. The solids were recovered by filtration and dried at 70° C. The mass was found to be 0.5 g. The selectivity and rates are shown in Table 1

Comparative Example 13

An inertised 450 ml autoclave was charged with methylcyclohexane (98 ml). In a Schlenk tube, a mixture of Cr(acac)$_3$ (2.5 µmol) and (o-ethylphenyl)$_2$PN(Me)P(o-ethylphenyl)$_2$ (2.5 µmol) in methylcyclohexane was treated with MMAO-3A (1.8 mmol Al). After stirring for 30 seconds, this mixture was added to the autoclave which was then pressurised to 30 bar (3000 kPa) ethylene. The mixture was stirred at 1100 r.p.m. to ensure thorough mass transfer. The uptake of ethylene into the autoclave was monitored, and the temperature and pressure were maintained at 60° C. and 30 bar (3000 kPa). After 13.5 minutes, the supply of ethylene was terminated and the autoclave was cooled to less than 25° C. and slowly depressurised. A sample of the liquid fraction was filtered and analysed by GC-FID. The mass of ethylene oligomers was found to be 127.5 g. The solids were recovered by filtration and dried at 70° C. The mass was found to be 21.1 g. The selectivity and rates are shown in Table 1

Example 14

An inertised 450 ml autoclave was fitted with a pressure vessel for solvent addition (see FIG. 2). The autoclave and pressure vessel were charged with methylcyclohexane (98 ml and 50 ml respectively) after which the pressure vessel containing the methylcyclohexane was pressurized to 30 bar (3000 kpa). In a Schlenk tube, a mixture of Cr(acac)$_3$ (2.5 µmol) and (o-ethylphenyl)$_2$PN(Me)P(o-ethylphenyl)$_2$ (2.5 µmol) in methylcyclohexane was treated with MMAO-3A (2.4 mmol Al). After stirring for 30 seconds, this mixture was added to the autoclave which was then pressurised to 30 bar (3000 kPa) ethylene. The mixture was stirred at 1100 r.p.m. to ensure thorough mass transfer. After ca 1.5 minutes of reaction time an additional aliquot of methylcyclohexane (46 ml) from the high pressure solvent pressure container was added to the autoclave under 30 bar (3000 kPa) ethylene pressure. The uptake of ethylene into the autoclave was monitored, and the temperature and pressure were maintained at 60° C. and 30 bar (3000 kPa). After 12.5 minutes, the supply of ethylene was terminated and the autoclave was cooled to less than 25° C. and slowly depressurised. A sample of the liquid fraction was filtered and analysed by GC-FID. The mass of ethylene oligomers was found to be 119.8 g. The solids were recovered by filtration and dried at 70° C. The mass was found to be 1.1 g. The selectivity and rates are shown in Table 1

Comparative Example 15

An inertised 300 ml autoclave was charged with toluene (100 ml). In a Schlenk tube, a solution of CrCl$_3$(bis-(2-decyl-sulfanyl-ethyl))-amine (0.012 mmol) was treated with Crompton MAO (1.7 mmol Al). After stirring for 10 seconds, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 90° C. and 45 bar (4500 kPa). After 30 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 36 g. The solids were recovered by filtration and dried at 70° C. The mass was found to be 0.25 g. The selectivity and rates are shown in Table 1.

Comparative Example 16

An inertised 300 ml autoclave was charged with toluene (100 ml). In a Schlenk tube, a solution of CrCl$_3$(bis-(2-decyl-sulfanyl-ethyl))-amine (0.012 mmol) was treated with Crompton MAO (0.48 mmol Al). After stirring for 10 seconds, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 90° C. and 45 bar (4500 kPa). After 30 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 19.0 g. The solids were recovered by filtration and dried at 70° C. The mass was found to be 0.7 g. The selectivity and rates are shown in Table 1.

Comparative Example 17

An inertised 300 ml autoclave was charged with toluene (100 ml). In a Schlenk tube, a solution of CrCl$_3$(bis-(2-decyl-sulfanyl-ethyl))-amine (0.008 mmol) was treated with Crompton MAO (1.14 mmol Al). After stirring for 10 seconds, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 90° C. and 45 bar (4500 kPa). After 30 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 20.0 g. The solids were recovered by filtration and dried at 70° C. The mass was found to be 1.04 g. The selectivity and rates are shown in Table 1.

Comparative Example 18

An inertised 300 ml autoclave was charged with toluene (100 ml). In a Schlenk tube, a solution of CrCl$_3$(bis-(2-decyl-sulfanyl-ethyl))-amine (0.026 mmol) was treated with Crompton MAO (1.48 mmol Al). After stirring for 10 seconds, this mixture was added to the autoclave which was then pressurised to 45 bar (4500 kPa) ethylene. The mixture was stirred at 1100 r.p.m. to ensure thorough mass transfer. The uptake of ethylene into the autoclave was monitored, and the temperature and pressure were maintained at 90° C. and 45 bar (4500 kPa). After 30 minutes, the supply of ethylene was terminated and the autoclave was cooled to less than 15° C. and slowly depressurised. A known mass of nonane was added as an internal standard. A sample of the liquid fraction was filtered and analysed by GC-FID. The mass of ethylene oligomers was found to be 37.89. The solids were recovered by filtration and dried at 70° C. The mass was found to be 0.25 g. The selectivity and rates are shown in Table 1

Example 19

An inertised 300 ml autoclave was fitted with a pressure vessel for solvent addition (see FIG. 2). The autoclave and pressure vessel were charged with toluene (98 ml and 50 ml respectively) after which the pressure vessel containing the toluene was pressurized to 45 bar (4500 kpa). In a schlenk, a solution of CrCl$_3$(bis-(2-decylsulfanyl-ethyl))-amine (0.026 mmol) was treated with Crompton MAO (1.48 mmol Al). After stirring for 10 seconds, this mixture was added to the autoclave which was then pressurised to 45 bar (4500 kPa) ethylene at 90° C. The mixture was stirred at 1100 r.p.m. to ensure thorough mass transfer. After ca 1.5 minutes of reaction time an additional aliquot of toluene (50 ml) from the high pressure solvent pressure container was added to the autoclave under 45 bar (4500 kPa) ethylene pressure. The uptake of ethylene into the autoclave was monitored, and the temperature and pressure were maintained at 90° C. and 45 bar (4500 kPa). After 30 minutes, the supply of ethylene was terminated and the autoclave was cooled to less than 25° C. and slowly depressurised. A sample of the liquid fraction was filtered and analysed by GC-FID. The mass of ethylene oligomers was found to be 34.6 g. The solids were recovered by filtration and dried at 70° C. The mass was found to be 0.2 g. The selectivity and rates are shown in Table 1

Comparative Example 20

An inertised 300 ml autoclave was charged with methylcyclohexane (97.2 ml). In a Schlenk tube, a mixture of Cr(2-ethylhexanoate)$_3$ (2.5 µmol) and (o-methoxyphenyl)2PN(Me)P(o-methoxyphenyl) (2.5 µmol) in methylcyclohexane (2.0 ml) was treated with MMAO-3A (1.8 mmol Al). After stirring for 30 seconds, this mixture was added to the autoclave which was then pressurised to 50 bar (5000 kPa) ethylene. The mixture was stirred at 1100 r.p.m. to ensure thorough mass transfer. The uptake of ethylene into the autoclave was monitored, and the temperature and pressure were maintained at 60° C. and 50 bar (5000 kPa). After 12 minutes, the supply of ethylene was terminated and the autoclave was cooled to less than 20° C. and slowly depressurised. A sample of the liquid fraction was filtered and analysed by GC-FID. The mass of ethylene oligomers was found to be 57.64 g. The solids were recovered by filtration and dried overnight at 70° C. The mass was found to be 0.2865 g. The selectivity and rates are shown in Table 1.

Comparative Example 21

An inertised 300 ml autoclave was charged with methylcyclohexane (98.7 ml). In a Schlenk tube, a mixture of Cr(2-ethylhexanoate)$_3$ (1.41 µmol) and (o-methoxyphenyl)2PN(Me)P(o-methoxyphenyl) (1.41 µmol) in methylcyclohexane (1.13 ml) was treated with MMAO-3A (0.677 mmol Al). After stirring for 30 seconds, this mixture was added to the autoclave which was then pressurised to 50 bar (5000 kPa) ethylene. The mixture was stirred at 1100 r.p.m. to ensure thorough mass transfer. The uptake of ethylene into the autoclave was monitored, and the temperature and pressure were maintained at 60° C. and 50 bar (5000 kPa). After 15 minutes, the supply of ethylene was terminated and the autoclave was cooled to less than 20° C. and slowly depressurised. A sample of the liquid fraction was filtered and analysed by GC-FID. The mass of ethylene oligomers was found to be 12.19 g. The solids were recovered by filtration and dried overnight at 70° C. The mass was found to be 1.1348 g. The selectivity and rates are shown in Table 1.

Comparative Example 22

An inertised 300 ml autoclave was charged with methylcyclohexane (97.5 ml). In a Schlenk tube, a mixture of Cr(2-ethylhexanoate)$_3$ (2.5 µmol) and (o-methoxyphenyl)2PN(Me)P(o-methoxyphenyl) (2.5 µmol) in methylcyclohexane (2.0 ml) was treated with trimethylaluminium (0.15 mmol, 0.8 mmol/L in methylcyclohexane) and MAO-HS (1.05 mmol Al, 3.6 mmol/L in toluene). After stirring for 30 seconds, this mixture was added to the autoclave which was then pressurised to 48 bar (4800 kPa) ethylene. The mixture was stirred at 1100 r.p.m. to ensure thorough mass transfer. The uptake of ethylene into the autoclave was monitored, and the temperature and pressure were maintained at 60° C. and 48 bar (4800 kPa). After 10 minutes, the supply of ethylene was terminated and the autoclave was cooled to less than 20° C. and slowly depressurised. A sample of the liquid fraction was filtered and analysed by GC-FID. The mass of ethylene oligomers was found to be 19.70 g. The solids were recovered by filtration and dried overnight at 70° C. The mass was found to be 0.2006 g. The selectivity and rates are shown in Table 1.

Comparative Example 23

An inertised 300 ml autoclave was charged with methylcyclohexane (98.7 ml). In a Schlenk tube, a mixture of Cr(2-ethylhexanoate)$_3$ (1.25 µmol) and (o-methoxyphenyl)2PN(Me)P(o-methoxyphenyl) (1.25 µmol) in methylcyclohexane (1.0 ml) was treated with trimethylaluminium (0.075 mmol, 0.8 mmol/L in methylcyclohexane) and MAO-HS (0.525 mmol Al, 3.6 mmol/L in toluene). After stirring for 30 seconds, this mixture was added to the autoclave which was then pressurised to 50 bar (5000 kPa) ethylene. The mixture was stirred at 1100 r.p.m. to ensure thorough mass transfer. The uptake of ethylene into the autoclave was monitored, and the temperature and pressure were maintained at 60° C. and 50 bar (5000 kPa). After 10 minutes, the supply of ethylene was terminated and the autoclave was cooled to less than 20° C. and slowly depressurised. A sample of the liquid fraction was filtered and analysed by GC-FID. The mass of ethylene oligomers was found to be 4.71 g. The solids were recovered by filtration and dried overnight at 70° C. The mass was found to be 0.4177 g. The selectivity and rates are shown in Table 1.

Example 24

An inertised 450 ml autoclave was fitted with a pressure vessel for solvent addition (see FIG. 2). The autoclave and pressure vessel were charged with methylcyclohexane (97.4 ml and 50 ml respectively) after which the pressure vessel containing the methylcyclohexane was pressurized to 45 bar (4500 kpa). In a Schlenk tube, a mixture of Cr(2-ethylhexanoate)$_3$ (2.5 µmol) and α-methoxyphenyl)2PN(Me)P(o-methoxyphenyl) (2.5 µmol) in methylcyclohexane (2.0 ml) was treated with MMAO-3A (1.2 mmol Al). After stirring for 30 seconds, this mixture was added to the autoclave which was then pressurised to 45 bar (4500 kPa) ethylene. The mixture was stirred at 1100 r.p.m. to ensure thorough mass transfer. After ca 1.5 minutes of reaction time, a further aliquot of methylcyclohexane (72 ml) from the high pressure solvent pressure container was added to the autoclave under 45 bar (4500 kPa) ethylene pressure. The uptake of ethylene into the autoclave was monitored, and the temperature and pressure were maintained at 60° C. and 45 bar (4500 kPa). After 13.0 minutes, the supply of ethylene was terminated and the autoclave was cooled to less than 25° C. and slowly depressurised. A sample of the liquid fraction was filtered and analysed by GC-FID. The mass of ethylene oligomers was found to be 55.5 g. The solids were recovered by filtration and dried at 70° C. The mass was found to be 0.3400 g. The selectivity and rates are shown in Table 1.

Comparative Examples 25-28

Continuous Stirred Tank Reactor

An inertised 2 liter autoclave equipped with gas entraining stirrer was connected via a control valve to a catch-pot (CP1) as shown in FIG. 3. The autoclave was equipped with an ethylene supply line, catalyst and MMAO supply line and a solvent supply line. The catalyst, MMAO and solvent were continuously fed to the autoclave (pressurised to 45 bar with ethylene) in the correct volumes to maintain the desired concentration of Cr and Al, shown in Table 1, within the reactor. The liquid volume (1 liter) was kept constant by continuously removing liquid to CP1, operating at a slightly reduced pressure. The catch pot was sampled every 20 minutes in order to calculate the solids and product make-up of the liquid which in turn was used to calculate the Cr efficiency.

Example 29

Dual-Continuous Stirred Tank Reactor

Two inertised autoclaves of volumes 300 ml (autoclave C) and 5 liters (autoclave D), both equipped with gas entraining stirrers, were connected via a dip-tube leading from autoclave C to autoclave D, in order to ensure a constant volume of 100 ml in autoclave C. The connecting pipe was equipped with a sampling point (SP1) such that samples from autoclave C could be drawn to determine the reaction rate and solids content of autoclave C, while autoclave D was connected via a control valve to catch pot (CP1) at a slightly lower pressure as shown in FIG. 4. Autoclave C was equipped with an ethylene supply line, catalyst and MMAO supply line and a solvent supply line (solvent 1) while autoclave D was only equipped with a solvent supply line (solvent 2). The catalyst, MMAO and solvent were continuously fed to autoclave C (pressurised to 45 bar with ethylene) to maintain the desired Cr and Al concentration in autoclave D, which in turn was transferred to autoclave D via the transfer line and subsequently diluted with solvent from the Solvent 2 line. The liquid volume (2.5 liters) in autoclave D was kept constant by continuously removing liquid to CP1, operating at a slightly reduced pressure. This experimental set-up allowed manipulation of the Cr and Al concentrations of each autoclave by varying the solvent feed rates to the respective autoclaves via the pumps (solvent 1 and solvent 2). The Cr and Al concentrations attained in autoclaves C and D are shown in Table 1. The catch pot was sampled every 20 minutes in order to calculate the solids and product make-up of the liquid which in turn was used to calculate the Cr efficiency of autoclave D. The same procedure was used to calculate the Cr efficiency of autoclave C by analyzing the samples taken at SP1.

TABLE 1

Rate and selectivity data for examples 1-29

| Example | Cr (µmol) | Al:Cr | $[Al]_{act}^{f}$ (mmol/L) | $[Al]_{cat}^{f}$ (mmol/L) | Efficiency (g/g Cr) | Rate (g/g Cr · h) | Solids (mass %) | 1-hexene (mass %) | 1-octene (mass %) |
|---|---|---|---|---|---|---|---|---|---|
| 1 [a,g] | 5.0 | 479 | 12.0 | 12.0 | 1201000 | 1638000 | 0.28 | 13.8 | 66.3 |
| 2 [a,g] | 5.0 | 479 | 12.0 | 12.0 | 1209000 | 1649000 | 0.32 | 14.3 | 66.1 |
| 3 [a,g] | 2.5 | 479 | 6.0 | 6.0 | 2411000 | 492000 | 2.19 | 15.1 | 64.3 |
| 4 [a,g] | 2.5 | 958 | 12.0 | 12.0 | 2252000 | 979000 | 0.42 | 14.8 | 65.3 |
| 5 [a,g] | 1.0 | 479 | 2.4 | 2.4 | 479000 | 240000 | 47.7 | 10.6 | 34.4 |
| 6 [a,g] | 1.0 | 2395 | 12.0 | 12.0 | 752000 | 376000 | 2.05 | 14.8 | 68.7 |
| 7 [b,g] | 3.0 [c] | 600 [d] | 24.0 | 6.0 | 1800000 | 3100000 | 0.4 | 15.5 | 65.5 |
| 8 [b,g] | 1.0 [c] | 870 [d] | 12.0 | 2.6 | 2800000 | 1400000 | 0.5 | 15.0 | 69.3 |
| 9 [b,g] | 1.1 [c] | 3800 [e] | 12.0 | 12.2 | 2100000 | 1000000 | 0.6 | 13.5 | 70.1 |
| 10 [h] | 2.5 | 960 | 24 | 24 | 1114203 | 4456811 | 0.86 | 88.4 | 2.2 |
| 11 [h] | 1.25 | 960 | 12 | 12 | 1821257 | 5463770 | 7.0 | 86.3 | 2.2 |
| 12 [h] | 1.25 | 1920 | 24 | 24 | 2056680 | 7051475 | 0.39 | 90.1 | 2.4 |
| 13 [h] | 2.5 | 720 | 18 | 18 | 1142763 | 5078949 | 14.1 | 78.1 | 1.8 |
| 14 [h] | 2.5 | 960 | 24 | 16.5 | 930141 | 4464677 | 0.9 | 88.6 | 1.8 |
| 15 [i] | 12.0 | 143 | 17.2 | 17.2 | 116188 | 58094 | 0.7 | 95.2 | 0.5 |
| 16 [i] | 12.0 | 57 | 6.8 | 6.8 | 30472 | 60945 | 3.7 | 92.3 | 0.6 |
| 17 [i] | 8.0 | 143 | 11.4 | 11.4 | 91349 | 45675 | 5.2 | 90.85 | 0.6 |
| 18 [i] | 26.0 | 57 | 14.8 | 14.8 | 27986 | 55972 | 0.7 | 94.9 | 0.6 |
| 19 [i] | 26.0 | 57 | 14.8 | 9.9 | 25576 | 51141 | 0.58 | 96.4 | 0.6 |
| 20 [j] | 2.5 | 720 | 18.0 | 18.0 | 445622 | 2228112 | 0.49 | 86.9 | 9.5 |
| 21 [j] | 1.41 | 480 | 6.8 | 6.8 | 180860 | 732441 | 8.51 | 80.6 | 9.6 |
| 22 [j] | 2.5 | 480 | 12.0 | 12.0 | 153076 | 918453 | 1.01 | 90.5 | 9.2 |
| 23 [j] | 1.25 | 480 | 6.0 | 6.0 | 78662 | 473173 | 8.15 | 89.7 | 8.5 |
| 24 [j] | 2.5 | 480 | 12.0 | 6.8 | 429515 | 1982377 | 0.61 | 85.1 | 8.6 |
| 25 [a,k] | 6.35 | 1887 | 12.0 | 12.0 | 752000 | 1050000 | 1.25 | 17.1 | 64.1 |
| 26 [a,k] | 7.7 | 1920 | 13.2 | 13.2 | 396000 | 540000 | 1.33 | 22.0 | 65.6 |
| 27 [a,k] | 10.2 | 1920 | 15.2 | 15.2 | 364000 | 408000 | 0.32 | 14.1 | 69.6 |

TABLE 1-continued

Rate and selectivity data for examples 1-29

| Example | Cr (μmol) | Al:Cr | $[Al]_{act}$[f] (mmol/L) | $[Al]_{cat}$[f] (mmol/L) | Efficiency (g/g Cr) | Rate (g/g Cr · h) | Solids (mass %) | 1-hexene (mass %) | 1-octene (mass %) |
|---|---|---|---|---|---|---|---|---|---|
| 28 [a,k] | 5.6 | 480 | 2.4 | 2.4 | 193000 | 389000 | 3.2 | 16.0 | 68.8 |
| 29 [k,l] | 38 [m] | 480 | 19 | 19 | 84500 [m] | 390000 [m] | Not measured | | |
| 29 [k,l] | 4.5 [n] | 480 | 19 | 2.2 | 431000 [n] | 660000 [n] | 0.8 | 15.5 | 69.2 |

[a] Activated in 1 liter reactor in full reaction volume
[b] Activated in 300 ml reactor; some of reaction mixture transferred to 1 litre reactor.
[c] Cr transferred into 1 liter reactor (estimated from amount of solvent transferred)
[d] Activated with Al:Cr = 479, additional Al present in 1 liter reactor as scavenger
[e] Activated with Al:Cr = 479, additional Al present in 1 liter reactor such that $[Al]_{cat}$~12 mmol/L.
[f] $[Al]_{act}$ is the Al concentration during activation of the catalyst by the activator in the presence of the olefin, but prior to dilution of the catalyst; whereas $[Al]_{cat}$ is the Al concentration subsequent to dilution of the catalyst. For examples 1-24, both $[Al]_{act}$ and $[Al]_{cat}$ does not take the dilution of the solvent with the dissolved reagent (ethylene) into account. For examples 25-29 both $[Al]_{act}$ and $[Al]_{cat}$ were calculated taking into account the dilution of the solvent with the dissolved reagent (ethylene).
[g] Examples 1-9 were conducted with Cr(acac)₃, (Ph₂P)₂N(iPropyl) (1.0 eq.), MMAO-3A in heptane (supplied by Akzo-Nobel) as cocatalyst, methylcyclohexane as solvent, 60° C., 45 bar ethylene.
[h] Examples 10-14 were conducted with Cr(acac)₃, (o-ethylphenyl)₂PN(Me)P(o-ethylphenyl)₂ (1.0 eq.), MMAO-3A in heptane as cocatalyst, methylcyclohexane as solvent, 60° C., 30 bar ethylene.
[i] Examples 15-19 were conducted with CrCl₃(bis-(2-decylsulfanyl-ethyl))-amine and MAO (supplied by Crompton) in toluene as cocatalyst, toluene as solvent, 90° C., 45 bar ethylene.
[j] Examples 20-24 were conducted with Cr(2-ethylhexanoate)₃, (o-methoxyphenyl)₂PN(Me)P(o-methoxyphenyl)₂ (1.0 eq.), MMAO-3A in heptane as cocatalyst, methylcyclohexane as solvent, 60° C., 50 bar ethylene.
[k] Examples 25, 27-29 were conducted with Cr(acac)₃, (Ph₂P)₂N(iPropyl) (1.0 eq.), MMAO-3A in heptane as cocatalyst, Isopar as solvent, 60° C., 45 bar ethylene. Comparative example 26 was conducted with (Ph₂P)₂N(1,2-dimethylpropyl) as ligand.
[l] Activated in 300 ml reactor; reaction mixture continuously transferred to 5 litre reactor.
[m] Autoclave C
[n] Autoclave D Discussion of Results The results are shown in Table 1. Examples 1-9 were included to highlight the concept of this invention using the Cr(acac)₃/(Ph₂P)₂N(iPropyl)/MMAO-3A oligomerisation catalyst system. Comparative examples 1 to 6 were activated in the full reaction volume of a 1 liter autoclave. Examples 1 and 2 demonstrate that with an Al:Cr ratio of 479, low solids formation can be achieved with this catalyst system, provided $[Al]_{act}$ and/or $[Al]_{cat}$ are at least 12 mmol/L. When the catalyst concentration (i.e. both [Al] and [Cr]) is reduced while maintaining Al:Cr of 479 (examples 3 and 5) the amount of solids produced increases dramatically. However when [Cr] was reduced, but [Al] maintained at 12.0 mmol/L (examples 4 and 6), much lower solids formation was observed. From these results it can be seen that within the boundaries of these working examples, the solids formation is not so much a function of low Al:Cr ratio or low [Cr], but is largely a function of low [Al].

Examples 7 and 8 were activated in the presence of an olefin (step A as defined above) with high $[Al]_{act}$ (≧12 mmol/L) and subsequent catalysis (step C as defined above) was performed at low $[Al]_{cat}$ (≦6 mmol/L), that is after dilution of the activated catalyst. It is clear from these results that low solids formation and good rates may be achieved despite a low $[Al]_{cat}$ in step C. In examples 7 and 8, solids of less than 0.5 mass % were achieved with low $[Al]_{cat}$ in step C (6.0 and 2.6 mmol/L respectively) as a result of activating in the presence of an olefin (step A) with high $[Al]_{cat}$ (24 and 12 mmol/L). The examples at comparable $[Al]_{cat}$ in step C but low $[Al]_{act}$ in step A (examples 3 and 5) gave 2.2 and 47.7% solids respectively. Example 9 using the same transfer procedure as examples 7 and 8 in which the $[Al]_{cat}$ in step C was increased to 12 mmol/L showed no benefit over example 8 (0.6% solids for example 9 v/s 0.5% for example 8).

Examples 10-24 serve to demonstrate that this concept is applicable to other oligomerisation catalysts based on different ligands, sources of transition metal and activators. Examples 10-13 (conducted with (o-ethylphenyl)₂PN(Me)P(o-ethylphenyl)₂ as ligand) were activated in the full liquid volume inside the 450 ml autoclave. Example 10 shows that with an Al:Cr of 960, low solids formation can be achieved with this catalyst, provided $[Al]_{cat}$ is at least 24 mmol/L. Examples 11 and 13 show that when the $[Al]_{act}$ is reduced below this value, significant amounts of solids are produced. Examples 11 and 12, in which the initial Cr charge is reduced from 2.5 to 1.25 μmol, show that high solids formation is not as a result of the lower [Cr] since low solids could be achieved by raising the [Al] from 12 mmol/L to 24 mmol/L. Examples 10 and 11 show that high solids formation is not as a result of Al:Cr since both experiments were carried out at an Al:Cr of 960, and only in the case where the $[Al]_{act}$ was 12 mmol/L, was high solids formation observed. In experiment 14 (also conducted with (o-ethylphenyl)₂PN(Me)P(o-ethylphenyl)₂ as ligand), $[Al]_{act}$ was 24 mmol/L and two minutes into the experiment, $[Al]_{cat}$ was reduced to 16.5 mmol/L through the addition of additional methylcyclohexane to the reactor. The rate and solids formation were very comparable to example 10, proving that good rates and low solids can be achieved despite a low $[Al]_{cat}$.

Comparative examples 15 and 17 (conducted using the CrCl₃(bis-(2-decylsulfanyl-ethyl))-amine/MAO catalyst system) demonstrate that by reducing the $[Al]_{cat}$ but also keeping the Al:Cr constant between runs, the amount of solids increases significantly, from 0.7% to 5.2%. Comparison of examples 15 and 16 shows that whilst keeping the [Cr] constant, and dropping the $[Al]_{cat}$ between runs, the amount of solids increases. Comparative examples 15-18 clearly show that solids formation is a function of low [Al], lower than 14.8 mmol/L of Al produces solids with this catalyst.

Examples 18 and 19 (also conducted using the (CrCl₃(bis-(2-decylsulfanyl-ethyl)-amine/MAO catalyst system) where both activated at $[Al]_{act}$=14.8 mmoldm⁻³. This concentration is not in the region where solids are produced, but for 19, the catalyst is diluted significantly subsequent to catalyst activation, so that the $[Al]_{cat}$ is considerably less than 14.8 mmol/L. In fact 19 yielded the lowest quantity of solids, confirming that low solids formation and good rates may be achieved despite the low $[Al]_{cat}$ if the system is activated at high $[Al]_{act}$ and subsequently diluted in situ.

Examples 20-24 serve to demonstrate that this invention is also applicable to the Cr(2-ethylhexanoate)$_3$(o-methoxyphenyl)$_2$PN(Me)P(o-methoxyphenyl)-$_2$-based trimerisation catalyst system.

Examples 1-24 were all batch examples using a variety of oligomerisation catalyst system. Examples 25-29 demonstrate that this invention is also applicable to oligomerisation under continuous operation with the Cr(acac)$_3$/(Ph$_2$P)$_2$N(iPropyl)/MMAO-3A catalyst system. In comparative examples 25-27, both [Al]$_{act}$ and [Al]$_{cat}$ were kept to $\geq$12 mmol/L. All three examples yielded less than 1.3% solids. In comparative example 28, both Al]$_{act}$ and [Al]$_{cat}$ was maintained at 2.4 mmol/L. This example yielded 3.2% solids (polymeric product). In example 29, the [Al]$_{act}$ was 19 mmol/L whereafter the catalyst was diluted with solvent so that [Al]$_{cat}$ was 2.4 mmol/L. Catalysis using this configuration yielded only 0.8 mass % solids.

The invention claimed is:

1. A process for producing an oligomeric product by the oligomerisation of at least one olefinic compound to be oligomerised, the at least one olefinic compound being in the form of an olefin or a compound including a carbon to carbon double bond, the process including:
   A) providing an activated oligomerisation catalyst comprising the combination of
      i) a source of Cr;
      ii) a ligating compound of the formula

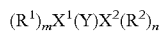
      $(R^1)_mX^1(Y)X^2(R^2)_n$ wherein: $X^1$ and $X^2$ are independently selected from the group consisting of N, P, As, Sb, Bi, O, S and Se;
      Y is a linking group between $X^1$ and $X^2$;
      m and n are independently 0, 1 or a larger integer; and
      $R^1$ and $R^2$ are independently hydrogen, a hydrocarbyl group or
      a heterohydrocarbyl group, and $R^1$ being the same or different
      when m>1, and $R^2$ being the same or different when n>1;
      iii) a metal containing activator, which is a compound selected from the group consisting of an alkylaluminoxane including methylaluminoxane (MAO), high stabilily methylaluminoxane (MAO HS), ethylaluminoxane (EAO), isobutylaluminoxane (iBuAO); and modified alkyialuminoxane including modified methylaluminoxane (MMAO); and
      iv) at least one olefinic compound in the form of an olefin or a compound including a carbon to carbon double bond; wherein components i) to iv), or one or more combinations thereof, have been combined in any suitable order to provide the activated oligomerisation catalyst;
   B) diluting the activated oligomerisation catalyst of A with an introduced liquid medium, that is a liquid medium that has not been formed in situ by the process for producing an oligomeric product; and
   C) contacting the at least one olefinic compound to be oligomerised with the diluted activated catalyst of B to produce an oligomeric product.

2. The process of claim 1 wherein the concentration of the metal of the metal containing activator in the activated catalyst prior to dilution is at least 3 mmol/l.

3. The process of claim 2 wherein the concentration of the metal of the metal containing activator in the activated catalyst prior to dilution is at least 12 mmol/l.

4. The process of claim 1 wherein the oligomerisation comprises trimerisation and/or tetramerisation of ethylene.

5. The process of claim 1 wherein the source of Cr is selected from the group consisting of chromium trichloride tris-tetrahydrofuran complex; (benzene)tricarbonyl chromium; chromium (III) octanoate; chromium hexacarbonyl; chromium (III) acetylacetonate, chromium (III) naphthenate, chromium (III) 2-ethylhexanoate.

6. The process of claim 5 wherein the source of Cr is chromium(III)acetylacetonate.

7. The process of claim 1 wherein the ligating compound is of the formula

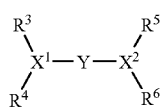

wherein $X^1$ and $X^2$ are independently selected from the group consisting of N, P, As, Sb and Bi; and $R^3$ to $R^6$ are each independently a hydrocarbyl group or a heterohydrocarbyl group.

8. The process of claim 7 wherein $X^1$ and $X^2$ are the same and both are P.

9. The process of claim 1 which includes a step of preparing the activated catalyst.

10. The process of claim 9 wherein the source of Cr (i), the ligating compound (ii) and the metal containing activator (iii) are first combined and subsequently contacted with the olefinic compound (iv).

11. The process of claim 10 which is carried out under conditions to allow oligomerisation of the olefinic compound (iv).

12. The process of claim 9 wherein the preparation of the activated catalyst is carried out in an inert liquid medium.

13. The process of claim 12 wherein the activated catalyst is diluted with the introduced liquid medium, in order to reduce the concentration of the metal containing activator before contacting the activated catalyst with the olefinic compound to be oligomerised.

14. The process of claim 13 wherein the introduced liquid medium is different from the oligomerisation product, and the introduced liquid medium is in the form of an inert liquid medium.

15. The process of claim 14 wherein, after dilution of the activated catalyst with the introduced liquid medium, the concentration of the metal containing activator is not above 6 mmol/l.

16. The process of claim 15 wherein the oligomerisation with the diluted activated catalyst is carried out at a pressure of above 1 bar.

17. The process of claim 16 wherein the oligomerisation with the diluted activated catalyst is carried out in an inert liquid medium.

18. The process of claim 1 wherein the olefinic compound (iv) is the same as the olefinic compound to be oligomerised.

19. The process of claim 18 wherein the olefinic compound (iv) is ethylene.

20. An oligomeric product produced by the process of claim 1.

* * * * *